(12) United States Patent
Wang

(10) Patent No.: US 9,107,917 B2
(45) Date of Patent: Aug. 18, 2015

(54) TREATMENT OF SEPSIS AND INFLAMMATION WITH ALPHA$_{2A}$ ADRENERGIC ANTAGONISTS

(75) Inventor: Ping Wang, Roslyn, NY (US)

(73) Assignee: The Feinstein Institute For Medical Research, Manhasset, NY (US)

( * ) Notice: Subject to any disclaimer, the term of this patent is extended or adjusted under 35 U.S.C. 154(b) by 1520 days.

(21) Appl. No.: 11/920,309

(22) PCT Filed: May 11, 2006

(86) PCT No.: PCT/US2006/018717
§ 371 (c)(1),
(2), (4) Date: Dec. 15, 2008

(87) PCT Pub. No.: WO2006/124770
PCT Pub. Date: Nov. 23, 2006

(65) Prior Publication Data
US 2009/0202518 A1 Aug. 13, 2009

Related U.S. Application Data

(60) Provisional application No. 60/680,999, filed on May 13, 2005.

(51) Int. Cl.
| | | |
|---|---|---|
| *A61K 31/415* | (2006.01) | |
| *A01N 43/50* | (2006.01) | |
| *A61K 31/4745* | (2006.01) | |
| *A61K 31/138* | (2006.01) | |
| *A61K 31/4164* | (2006.01) | |
| *A61K 31/417* | (2006.01) | |
| *A61K 31/4174* | (2006.01) | |
| *A61K 31/4178* | (2006.01) | |
| *A61K 31/475* | (2006.01) | |
| *A61K 31/496* | (2006.01) | |
| *A61K 31/506* | (2006.01) | |

(52) U.S. Cl.
CPC ........... *A61K 31/4745* (2013.01); *A61K 31/138* (2013.01); *A61K 31/417* (2013.01); *A61K 31/4164* (2013.01); *A61K 31/4174* (2013.01); *A61K 31/4178* (2013.01); *A61K 31/475* (2013.01); *A61K 31/496* (2013.01); *A61K 31/506* (2013.01)

(58) Field of Classification Search
CPC ............ A61K 2300/00; A61K 31/138; A61K 31/4164; A61K 31/417; A61K 31/4174; A61K 31/4178; A61K 31/475; A61K 31/496; A61K 31/506; A61K 31/4745
USPC ........................................................ 514/397
See application file for complete search history.

(56) References Cited

U.S. PATENT DOCUMENTS

| | | | |
|---|---|---|---|
| 5,069,911 A | 12/1991 | Zuger | |
| 5,661,172 A | 8/1997 | Colpaert et al. | |
| 5,674,836 A * | 10/1997 | Kilbourn et al. | ................ 514/2.4 |
| 6,472,181 B1 | 10/2002 | Mineau-Hanschke | ....... 435/70.3 |
| 6,489,296 B1 * | 12/2002 | Grinnell et al. | ............ 424/94.64 |
| 6,514,934 B1 * | 2/2003 | Garvey et al. | ................ 514/20.6 |
| 2005/0049256 A1 | 3/2005 | Lorton et al. | |

FOREIGN PATENT DOCUMENTS

EP 1086695 A1 3/2001

OTHER PUBLICATIONS

Maestroni, J of Neuroimmunology 144, 2003, 91-99.*
Remington's Pharmaceutical Sciences, 1980, Sixteenth Edition, p. 420-425.*
Wenzel et al. (Clinical Infectious Disease, 1996, 22, 407-13).*
Rao (Intensive Care Med, 1998, 283-285).*
Rascol (Movement Disorders, 16, 4, 2001).*
Yang et al. (Am J of Physiol Gastrointest Liver Physiology G1014-G1021, 2001).*
Yohimbe (American Cancer Society, Yohimbe, 2008).*
Kearney (Ann Pharmacotherapy 2010, p. 1-2).*
Zhou et al (Biochimica Biophysica Acta, 1537, 2001, 49-57).*
Merck, 2008, Sepsis and Septic Shock.*
Sepsis (http://my.clevelandclinic.org/health/diseases_conditions/hic_Sepsis, 2011).*
The International Preliminary Report on Patentability for PCT Application No. PCT/US2006/018717, dated Nov. 22, 2007.
Mason et al, May 2003, Molecular Therapy, 7(5): S404.
Kamata et al, 2004, J Oral Pathol Med, 33(7): 417-423.
Gysin et al, 2002, Gene Therapy, 9: 991-999.
Shi et al, 2007, European Journal of Neuroscience, 26: 3016-3023.
Wells (Sep. 18, 1990) "Additivity of Mutational Effects in Proteins." Biochemistry 29(37): 8509-8517.
Ngo et al. (Mar. 2, 1995) The protein Folding problem and Tertiary Structure Prediction, Chapter 14: Computational Complexity Protein Structure Prediction, and the Levinthal.
Wang et al. (Nuc. Acids Res. 27: 4609-4618, 1999; p. 4617).
Kaufman et al (Blood 94: 3178-3184, 1999).
Phillips, A., J Pharm Pharmacology 53: 1169-1174, 2001.
U.S. Appl. No. 11/588,768 Office Action dated Sep. 15, 2008.
U.S. Appl. No. 11/588,768 Office Action dated Jun. 8, 2009.

(Continued)

*Primary Examiner* — Uma Ramachandran
(74) *Attorney, Agent, or Firm* — Amster, Rothstein & Ebenstein LLP

(57) ABSTRACT

Provided are methods for treating a mammal undergoing sepsis, or at risk for sepsis. Also provided are methods of preventing or treating a physiological effect of sepsis in a mammal. Additionally provided are methods of inhibiting an inflammatory response in a mammal. Further provided is the use of an $\alpha_{2A}$-adrenergic antagonist for the manufacture of a medicament for preventing or treating a physiologic effect of sepsis in a mammal, and the use of an $\alpha_{2A}$-adrenergic antagonist for the treatment of a mammal having sepsis or at risk for sepsis.

4 Claims, 1 Drawing Sheet

(56) References Cited

OTHER PUBLICATIONS

U.S. Appl. No. 11/588,768 Final Office Action dated Jan. 19, 2010.
European Office Action dated Feb. 22, 2013 corresponding to European Patent Application No. 06 770 364.5-1453.
Certificate of Patent for Invention in corresponding Chinese Application No. 200680022383.6 granted Oct. 10, 2012.
European Office Action dated Jul. 30, 2012 corresponding to European Patent Application No. 06 770 364.5.
The International Search Report and the Written Opinion of the International Searching Authority of PCT Application No. PCT/US2006/018717, 2006.
Dellinger, "Current Therapy for Sepsis." Infect. Dis. Clin. North Am. 1999, 13:2, pp. 495-509.
Supplementary European Search Report dated Jun. 12, 2012, corresponding to European Patent Application No. 06770364.5.
Das, P., et al. "Important Role in TNF-[alpha] Release in Sepsis.: 88," which was Cited in the Supplementary European Search Report dated Jun. 12, 2012, corresponding to European Patent Application No. 06770364.5.
Zhou, Mian, et al. "Gut-Derived Norepinephrine Plays an Important Role in Up-Regulating IL-1β and IL-10," Biochimica et Biophysics Acta 1740 (2005) 446-452, which was cited in the Supplementary European Search Report dated Jun. 12, 2012, corresponding to European Patent Application No. 06770364.5.
Zhou, Mian, et al. "Adrenomedullin and Adrenomedullin Binding Protein-1 Attenuate Vascular Endothelial Cell Apoptosis in Sepsis." Annals of Surgery, vol. 240, No. 2, Aug. 2004 which was cited in the Supplementary European Search Report dated Jun. 12, 2012, corresponding to European Patent Application No. 06770364.5.

\* cited by examiner

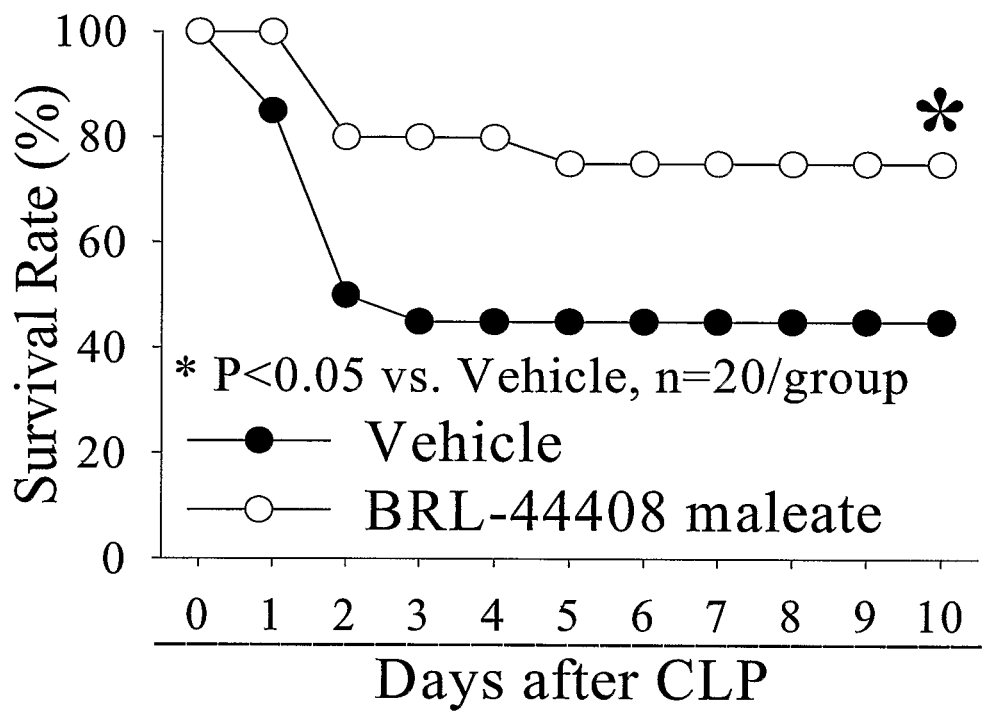

TREATMENT OF SEPSIS AND INFLAMMATION WITH ALPHA$_{2A}$ ADRENERGIC ANTAGONISTS

CROSS-REFERENCE TO RELATED APPLICATION

This is a U.S. national phase of PCT Application No. PCT/US2006/018717, filed May 11, 2006 and claims priority to U.S. Provisional Application No. 60/680,999, filed May 13, 2005.

STATEMENT REGARDING FEDERALLY SPONSORED RESEARCH OR DEVELOPMENT

This invention was made with government support under grant number GM053008 awarded by the National Institutes of Health. The government has certain rights in the invention.

BACKGROUND OF THE INVENTION (1) Field of the Invention

The present invention generally relates to treatments of sepsis and inflammation. More specifically, the invention is directed to the use of $\alpha_{2A}$-adrenergic antagonists to treat sepsis and inflammatory diseases.

(2) Description of the Related Art

Despite advances in the management of trauma victims, the incidence of sepsis and septic shock has increased significantly over the past two decades. It has been estimated that in the United States alone, more than 750,000 patients develop sepsis and septic shock each year with an overall mortality rate of 28.6%. Severe sepsis is a common, expensive, and frequently fatal condition, with as many deaths annually as those from acute myocardial infarction. Sepsis is the 3rd leading cause of death overall in the United States. A recent report indicates that the average costs per septic patient are at least $22,100, with annual total costs of more than $16 billion nationally. Activated protein C (APC) is the only FDA-approved specific treatment for sepsis, but its use is limited to non-surgical adult patients with severe sepsis. APC cannot be used in trauma victims and surgical patients who develop sepsis, due to its adverse effects on coagulation. Thus, there is a great need for an effective novel therapy for sepsis, especially surgical sepsis. The market potential for sepsis treatment is estimated at $10-25 billion annually in the United States alone.

SUMMARY OF THE INVENTION

Accordingly, the inventor has discovered that treating a mammal with an $\alpha_{2A}$-adrenergic antagonist can prevent or reduce physiologic effects of sepsis and inflammation.

Thus, in some embodiments, the invention is directed to methods of treating a mammal undergoing sepsis. The methods comprise treating the mammal with an $\alpha_{2A}$-adrenergic antagonist such that a physiologic effect of the sepsis is prevented or reduced.

In other embodiments, the invention is directed to methods of treating a mammal at risk for sepsis. The methods comprise treating the mammal with an $\alpha_{2A}$-adrenergic antagonist sufficient to prevent or reduce a physiologic effect of the sepsis.

The present invention is additionally directed to methods of preventing or treating a physiologic effect of sepsis in a mammal. The methods comprise treating the mammal with an $\alpha_{2A}$-adrenergic antagonist such that a physiologic effect of the sepsis is prevented or reduced.

The invention is also directed to methods of inhibiting an inflammatory response in a mammal, where the inflammatory response is mediated by a proinflammatory cytokine. The methods comprise treating the mammal with an $\alpha_{2A}$-adrenergic antagonist sufficient to inhibit the inflammatory response.

Additionally, the invention is directed to the use of an $\alpha_{2A}$-adrenergic antagonist for the manufacture of a medicament for preventing or treating a physiologic effect of sepsis in a mammal.

In further embodiments, the invention is directed to the use of an $\alpha_{2A}$-adrenergic antagonist for the treatment of a mammal having sepsis or at risk for sepsis.

BRIEF DESCRIPTION OF THE DRAWING

FIG. 1 is a graph of experimental results showing increased survival of rats undergoing sepsis when treated with the $\alpha_{2A}$-adrenergic antagonist BRL-44408 maleate.

DETAILED DESCRIPTION OF THE INVENTION

The present invention is based in part on the inventor's discovery that treating a mammal with an $\alpha_{2A}$-adrenergic antagonist can prevent or reduce physiologic effects of sepsis and inflammation. See Example.

Thus, in some embodiments, the present invention is directed to methods of treating a mammal undergoing sepsis. The methods comprise treating the mammal with an $\alpha_{2A}$-adrenergic antagonist such that a physiologic effect of the sepsis is prevented or reduced.

These methods are expected to be effective with any $\alpha_{2A}$-adrenergic antagonist now known or later discovered. Non-limiting examples of $\alpha_{2A}$-adrenergic antagonists that are encompassed within these embodiments are BRL-44408 maleate, RX821002, rauwolscine, idazoxan, piribedil, atipamezole, dihydroergotamine, phentolamine, phenoxybenzamine, tolazoline, ARC 239, efaroxan, RS 79948, spiroxatrine, and yohimbine. The selection of $\alpha_{2A}$-adrenergic antagonist can be made by the skilled artisan without undue experimentation, taking into account, e.g., the selectivity and side effects of the compound and the sensitivity or hypersensitivity of the mammal to the compound. In some preferred embodiments, the $\alpha_{2A}$-adrenergic antagonist is BRL-44408 maleate. The $\alpha_{2A}$-adrenergic antagonist can also be an antibody or an aptamer, which can be made by routine methods well known in the art.

For all embodiments of the present invention, the $\alpha_{2A}$-adrenergic antagonist, or a salt thereof, is preferably formulated in a pharmaceutical composition. These compositions can be formulated without undue experimentation for administration to a mammal, including humans, as appropriate for the particular application. Additionally, proper dosages of the compositions can be determined without undue experimentation using standard dose-response protocols.

Accordingly, the compositions designed for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The compositions of the present invention can easily be administered parenterally such as for example, by intravenous, intramuscular, intrathecal or subcutaneous injection. Parenteral administration can be accomplished by incorporating the compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches (such as the well-known nicotine patch), ointments, creams, gels, salves and the like.

The present invention includes nasally administering to the mammal a therapeutically effective amount of the composition. As used herein, nasally administering or nasal administration includes administering the composition to the mucous membranes of the nasal passage or nasal cavity of the patient. As used herein, pharmaceutical compositions for nasal administration of a composition include therapeutically effective amounts of the composition prepared by well-known methods to be administered, for example, as a nasal spray, nasal drop, suspension, gel, ointment, cream or powder. Administration of the composition may also take place using a nasal tampon or nasal sponge.

The methods of the present invention prevent or reduce any physiologic effect of sepsis, including shock (which in turn affects endothelial cell function, smooth muscle contractility, cardiac output, stroke volume, systemic oxygen delivery, lactic acidosis, hemoconcentration, total peripheral vascular resistance and/or regional blood perfusion), renal function, hepatic function, gut absorptive function, adrenal function, insulin responsiveness, altered cytokine (e.g., IL-10, TNF-$\alpha$, IL-1$\beta$ and/or IL-6) release, and physiological effects of altered cytokine release (e.g., inflammation). To evaluate the prevention or reduction of physiologic effects of sepsis, it is preferred that physiologic effects that are easily measured are compared before and after treatment. Examples of these effects are elevation of serum TNF-$\alpha$ levels, elevation of serum ALT levels, elevation of serum AST levels, elevation of serum lactate, and elevation of serum creatinine. In preferred embodiments, the measured physiological effect of the sepsis is elevation of serum TNF-$\alpha$ levels. Determination of shock, or its direct effects (e.g., hemoconcentration, peripheral vascular resistance, etc.) is also easily measured and can be utilized.

These methods can also comprise treating the mammal with a second treatment that can reduce a physiological effect of the sepsis. Examples of such treatments include administration of adrenomedullin, adrenomedullin binding protein, activated protein C, or milk fat globule epidermal growth factor-factor VIII. The latter treatment is described in U.S. Provisional Patent Application 60/680,628, titled MILK FAT GLOBULE EPIDERMAL GROWTH FACTOR VIII AND SEPSIS, filed May 13, 2005.

In other embodiments, the invention is directed to methods of treating a mammal at risk for sepsis. The methods comprise treating the mammal with an $\alpha_{2A}$-adrenergic antagonist sufficient to prevent or reduce a physiologic effect of the sepsis. As with the methods described above, these embodiments are not limited to any particular $\alpha_{2A}$-adrenergic antagonists. Examples of useful $\alpha_{2A}$-adrenergic antagonists are BRL-44408 maleate, RX821002, rauwolscine, idazoxan, piribedil, atipamezole, dihydroergotamine, phentolamine, phenoxybenzamine, tolazoline, ARC 239, efaroxan, RS 79948, spiroxatrine, and yohimbine. In some preferred embodiments, the $\alpha_{2A}$-adrenergic antagonist is BRL-44408 maleate. The $\alpha_{2A}$-adrenergic antagonist can also be an antibody or an aptamer, as discussed above.

These methods can also comprise treating the mammal with a second treatment that can reduce a physiological effect of the sepsis. Examples of such treatments include administration of adrenomedullin, adrenomedullin binding protein, activated protein C, or milk fat globule epidermal growth factor-factor VIII.

The methods of the present invention prevent or reduce any physiologic effect of sepsis, including shock and TNF-$\alpha$ levels.

The present invention is also directed to methods of preventing or treating a physiologic effect of sepsis in a mammal. The methods comprise treating the mammal with an $\alpha_{2A}$-adrenergic antagonist such that a physiologic effect of the sepsis is prevented or reduced.

As with the methods described above, these embodiments are not limited to any particular $\alpha_{2A}$-adrenergic antagonists. Examples of useful $\alpha_{2A}$-adrenergic antagonists are BRL-44408 maleate, RX821002, rauwolscine, idazoxan, piribedil, atipamezole, dihydroergotamine, phentolamine, phenoxybenzamine, tolazoline, ARC 239, efaroxan, RS 79948, spiroxatrine, and yohimbine. In some preferred embodiments, the $\alpha_{2A}$-adrenergic antagonist is BRL-44408 maleate. The $\alpha_{2A}$-adrenergic antagonist can also be an antibody or an aptamer, as discussed above.

These methods can also comprise treating the mammal with a second treatment that can reduce a physiological effect of the sepsis. Examples of such treatments include administration of adrenomedullin, adrenomedullin binding protein, activated protein C, or milk fat globule epidermal growth factor-factor VIII.

The methods of the present invention prevent or reduce any physiologic effect of sepsis, including shock and TNF-$\alpha$ levels.

Since $\alpha_{2A}$-adrenergic antagonists reduce TNF-$\alpha$ levels, treatment with $\alpha_{2A}$-adrenergic antagonists are effective to reduce inflammatory responses mediated by proinflammatory cytokines, since such responses generally are mediated in large part by TNF-α. Thus, the invention is also directed to methods of inhibiting an inflammatory response in a mammal, where the inflammatory response is mediated by a proinflammatory cytokine. These methods comprise treating the mammal with an $\alpha_{2A}$-adrenergic antagonist sufficient to inhibit the inflammatory response.

As with the methods described above, these embodiments are not limited to any particular $\alpha_{2A}$-adrenergic antagonists. Examples of useful $\alpha_{2A}$-adrenergic antagonists are BRL-44408 maleate, RX821002, rauwolscine, idazoxan, piribedil, atipamezole, dihydroergotamine, phentolamine, phenoxybenzamine, tolazoline, ARC 239, efaroxan, RS 79948, spiroxatrine, and yohimbine. In some preferred embodiments, the $\alpha_{2A}$-adrenergic antagonist is BRL-44408 maleate. The $\alpha_{2A}$-adrenergic antagonist can also be an antibody or an aptamer, as discussed above.

In preferred embodiments, the proinflammatory cytokine is TNF-α.

In other preferred embodiments, the mammal is suffering from, or at risk for, a condition mediated by an inflammatory cytokine cascade. Nonlimiting examples of such conditions include appendicitis, peptic, gastric and duodenal ulcers, peritonitis, pancreatitis, ulcerative, pseudomembranous, acute and ischemic colitis, diverticulitis, epiglottitis, achalasia, cholangitis, cholecystitis, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopicsilicovolcanoconiosis, alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, demmatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, Type I diabetes, ankylosing spondylitis, Berger's disease, Type I diabetes, ankylosing spondylitis, Berger's disease, Retier's syndrome, or Hodgkins disease. Preferably, the condition is appendicitis, peptic, gastric and duodenal ulcers, peritonitis, pancreatitis, ulcerative, pseudomembranous, acute and ischemic colitis, hepatitis, Crohn's disease, asthma, allergy, anaphylactic shock, organ ischemia, reperfusion injury, organ necrosis, hay fever, sepsis, septicemia, endotoxic shock, cachexia, septic abortion, disseminated bacteremia, burns, Alzheimer's disease, coeliac disease, congestive heart failure, adult respiratory distress syndrome, cerebral infarction, cerebral embolism, spinal cord injury, paralysis, allograft rejection and graft-versus-host disease. In the most preferred embodiments, the condition is septic shock.

The present invention is also directed to the use of an $\alpha_{2A}$-adrenergic antagonist for the manufacture of a medicament for preventing or treating a physiologic effect of sepsis in a mammal. As with the methods described above, these embodiments are not limited to any particular $\alpha_{2A}$-adrenergic antagonists. Examples of useful $\alpha_{2A}$-adrenergic antagonists are BRL-44408 maleate, RX821002, rauwolscine, idazoxan, piribedil, atipamezole, dihydroergotamine, phentolamine, phenoxybenzamine, tolazoline, ARC 239, efaroxan, RS 79948, spiroxatrine, and yohimbine. In some preferred embodiments, the $\alpha_{2A}$-adrenergic antagonist is BRL-44408 maleate. The $\alpha_{2A}$-adrenergic antagonist can also be an antibody or an aptamer, as discussed above.

In related embodiments, the invention is additionally directed to the use of an $\alpha_{2A}$-adrenergic antagonist for the treatment of a mammal having sepsis or at risk for sepsis.

As with the methods described above, these embodiments are not limited to any particular $\alpha_{2A}$-adrenergic antagonists. Examples of useful $\alpha_{2A}$-adrenergic antagonists are BRL-44408 maleate, RX821002, rauwolscine, idazoxan, piribedil, atipamezole, dihydroergotamine, phentolamine, phenoxybenzamine, tolazoline, ARC 239, efaroxan, RS 79948, spiroxatrine, and yohimbine. In some preferred embodiments, the $\alpha_{2A}$-adrenergic antagonist is BRL-44408 maleate. The $\alpha_{2A}$-adrenergic antagonist can also be an antibody or an aptamer, as discussed above.

In preferred embodiments, the proinflammatory cytokine is TNF-α.

Preferred embodiments of the invention are described in the following example. Other embodiments within the scope of the claims herein will be apparent to one skilled in the art from consideration of the specification or practice of the invention as disclosed herein. It is intended that the specification, together with the example, be considered exemplary only, with the scope and spirit of the invention being indicated by the claims, which follow the example.

Example 1

The nervous system regulates the inflammatory response in real time. Our previous studies have shown that the sympathetic neurotransmitter, norepinephrine (NE), increases TNF-α release via activation of $\alpha_{2A}$-adrenoceptor ($\alpha_{2A}$-AR) on Kupffer cells (KCs). In cultured KCs, NE increases the release of TNF-α by 3.4-fold and a specific antagonist for $\alpha_{2A}$-AR, BRL-44408 maleate, reduces TNF-α secretion by 51%. However, it remains unknown whether in vivo administration of $\alpha_{2A}$-AR antagonists in sepsis is beneficial.

Sepsis was induced in male rats by cecal ligation and puncture (CLP). The CLP model of sepsis has been used extensively as a reliable model of the pathophysiologic and immunologic alterations in human sepsis.

BRL-44408 maleate (2.5 mg/kg BW) was administered intravenously at the time of CLP. Twenty hours after CLP, the rats were sacrificed and blood and liver samples were collected. Serum levels of TNF-α, liver enzymes (i.e., AST and ALT), lactate and creatinine were measured. Gene expression of TNF-α in the liver was analyzed. In additional groups of animals, the necrotic cecum was excised at 20 h post-CLP and the 10-day survival was recorded. The results (means±SE) are shown in Table 1.

TABLE 1

|  | Sham Control | CLP Vehicle | CLP BRL-44408 maleate |
|---|---|---|---|
| TNF-α (pg/ml) | 65.8 ± 8.2 | 160 ± 25.2* | 91.8 ± 8.1# |
| TNF-α/G3PDH (mRNA) | 0.2 ± 0.01 | 1.4 ± 0.3* | 0.5 ± 0.1# |
| ALT (IU/L) | 8.5 ± 3.1 | 40.9 ± 4.4* | 20.5 ± 4.5# |
| AST (IU/L) | 13.6 ± 2.1 | 55.7 ± 7.7* | 20.9 ± 5.3# |
| Lactate (mg/dl) | 10.8 ± 0.9 | 32.6 ± 2.1* | 20.6 ± 1.9# |
| Creatinine (mg/dl) | 0.8 ± 0.2 | 2.3 ± 0.4* | 1.1 ± 0.2*# |

One-way ANOVA:
*P < .05 vs. Sham;
P < .05 vs. Vehicle, n = 6/group

Our results indicate that BRL-44408 maleate administration decreased the expression of TNF-α, attenuated tissue injury (Table 1), and reduced mortality (FIG. 1) in septic animals. Thus, modulation of the sympathetic nervous system by blocking $\alpha_{2A}$-adrenergic receptors appears to be a novel treatment for inflammatory conditions such as sepsis.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method of attenuating sepsis in a mammal, the method comprising administering to the mammal an amount of an $\alpha_{2A}$-specific-adrenergic antagonist compound that is BRL-44408, or a salt thereof, which attenuates sepsis.

2. The method of claim 1, wherein the $\alpha_{2A}$-specific-adrenergic-antagonist compound is BRL-44408 maleate.

3. The method of claim 1, further comprising treating the mammal with an amount of adrenomedullin, adrenomedullin binding protein, activated protein C, or milk fat globule epidermal growth factor-factor VIII that can reduce a physiological effect of the sepsis.

4. The method of claim 1, wherein the mammal is a human.

* * * * *